United States Patent [19]

Hakki

[11] Patent Number: 4,549,557
[45] Date of Patent: Oct. 29, 1985

[54] PACEMAKER ELECTRODE

[76] Inventor: A-Hadi I. Hakki, 1536 Woodland Ave., Folcroft, Pa. 19032

[21] Appl. No.: 547,605

[22] Filed: Nov. 1, 1983

[51] Int. Cl.$^4$ .............................................. A61N 1/04
[52] U.S. Cl. .................................... 128/785; 128/642
[58] Field of Search ............... 128/785, 784, 786, 787, 128/788, 789, 642, 419 P

[56] References Cited

U.S. PATENT DOCUMENTS

| | | | |
|---|---|---|---|
| 3,902,501 | 9/1975 | Citron et al. | 128/419 P |
| 4,058,128 | 11/1977 | Frank et al. | 128/785 |
| 4,136,702 | 1/1979 | Trabucco | 128/419 P |

Primary Examiner—Kyle L. Howell
Assistant Examiner—David Shay
Attorney, Agent, or Firm—Seidel, Gonda, Goldhammer

[57] ABSTRACT

An improved pacemaker electrode has a plurality of flexible barbs at the end thereof which is inserted into the human heart. Each barb is provided with at least one opening through which heart tissue can grow to anchor the electrode in the heart. Each barb also has a rear rib bifurcated by a gap which communicates with the rearmost opening in the barb. The gap allows the trabeculae to be trapped acutely in the opening during initial insertion to prevent the tip from becoming dislodged.

6 Claims, 5 Drawing Figures

PACEMAKER ELECTRODE

BACKGROUND OF THE INVENTION

The rate and rhythm of the heart are controlled by a small collection of specialized nervous tissue known as the sinuatrial node, situated at the base of the heart. This is the natural pacemaker of the heart-or cardiac pacemaker. When the impulse sent out by this pacemaker cannot reach all parts of the heart (a condition known as heart-block), the heart either stops or contracts in an irregular manner.

In these cases, the natural pacemaker can be replaced by an artificial pacemaker which, for all practical purposes, is a battery which stimulates the heart and allows it to beat at normal speeds. The pacemaker generates controlled, periodic, direct electric potentials (pulse voltages) through electrodes buried in a patient's chest (reaching the heart area). Thousands of encapsulated, implantable pacemakers are in use throughout the nation today. In addition, temporary externally-worn pacemakers are in use which are either fixed to the outside of the chest or upper or lower extremity and connected to an electrode catheter which is passed through a vein into the appropriate heart chamber.

Problems often arise in respect to the placement and anchoring of the pacemaker electrodes. Unless the electrode is properly anchored during initial insertion, it can pull out of the heart tissue. Obviously, if it does so, the heart can no longer be stimulated by the pacemaker. The result is cardiac arrythmia or cardiac arrest, or emergence of the underlying rhythm because of pacemaker malfunction.

As shown in FIG. 1, prior art electrodes are provided with barbs to facilitate insertion of the probe into the heart tissue. The barbs are provided with openings through which heart tissue can grow once the electrodes are in place to thereby anchor the electrode. The main drawback of the prior art electrodes is that it takes a considerable amount of time for new heart tissue to grow around the electrode and through the opening of the barbs to permanently anchor the electrode in place. Until a sufficient amount of tissue has grown through the openings, the electrode can easily become dislodged.

The present invention prevents the electrode from becoming dislodged during initial insertion. A barb traps the trabeculae in the heart acutely during initial insertion and thereby holds the electrode firmly in place until sufficient heart tissue has grown around the electrode to anchor it permanently.

SUMMARY OF THE INVENTION

An electrode for insertion into the human heart has an electrically conductive contact at its distal end. A flexible electric conductor is connected to the contact and is encased in an insulting sheath rearward of the contact. A plurality of flexible barbs are located adjacent the contact. Each barb has at least one opening through it. The rear rib of each barb is bifurcated by a gap which communicates with the rearmost opening through the barb.

The barb in the rear rib enables the trabeculae to be trapped acutely in the rearmost opening of the barb during initial insertion and prevents the electrode from becoming dislodged. Clinical testing on laboratory animals has indicated that the electrode of the present invention is considerably more likely to remain in place than electrodes of the prior art design.

DETAILED DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
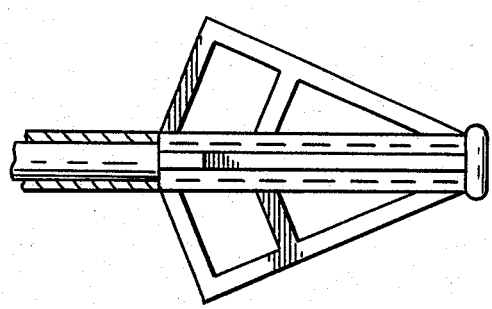
FIG. 1 is a partial cross-section of a pacemaker electrode of the prior art.
Figure 2:
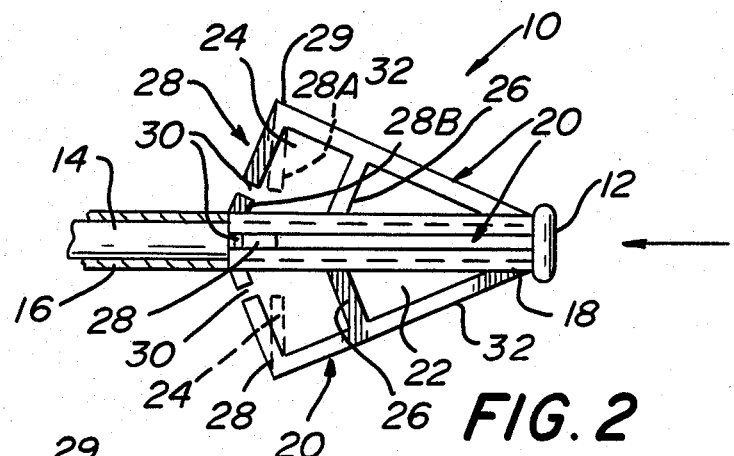
FIG. 2 is a partial cross-section of a pacemaker electrode in accordance with the present invention.

Referring to the drawings, wherein like numerals indicate like elements, there is shown in FIG. 2 a pacemaker electrode 10 in accordance with the present invention. The electrode has a tubular collar 18 which terminates at one end in a bulbous tip or contact 12. The opposite end of collar 18 is open.

Collar 18 fits over a flexible conductor 14 which is attached both mechanically and electrically to collar 18 by any suitable means such as crimping or soldering. Flexible conductor 14 is flexible enough and of sufficient length to enable the pacemaker electrode 10 to be used with either internal or external pacemakers located in close promixity to or at some distance from the heart.

Figure 4:
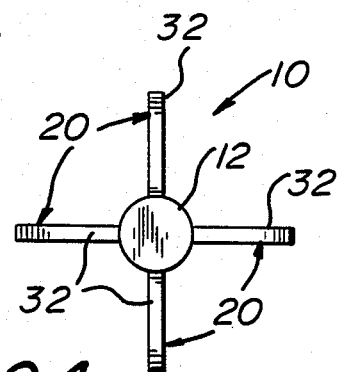
FIG. 4 is an end view of the electrode shown in FIG. 2.
Figure 5:
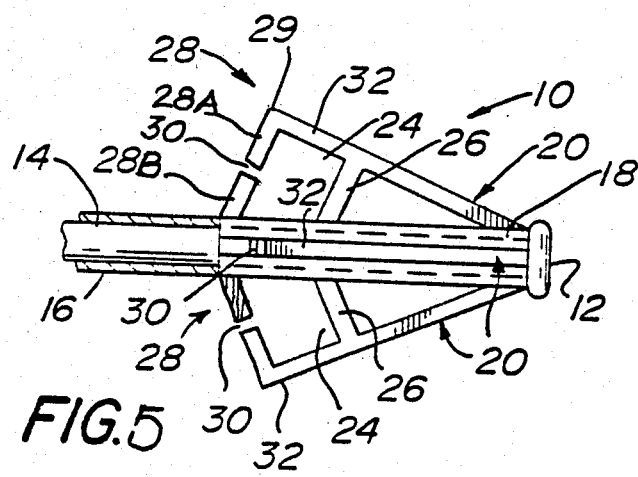
FIG. 5 is a partial cross-section of a third embodiment of the invention.

Rearward of tip 12, collar 18 and flexible conductor 14 are encased in an insulating sheath 16 made of flexible, non-conductive material. Integral with the insulating sheath 16 are a plurality of flexible barbs 20. As best seen in FIG. 4, barbs 20 are disposed behind tip 12 in planes which intersect the longitudinal axis of the tubular collar 18. As shown in FIG. 2, each barb has a forward cut-out 22 and a rear cut-out 24 which are separated by mid-rib 26. Although two cut-outs are presently preferred and are illustrated, it should be appreciated that other numbers of cut-outs may be used without departing from the scope of the present invention.

Each barb has a forward arm 32 and a rear rib 28. The rear rib 28 of each barb 20 is bifurcated by a gap 30 into two flexible rib elements 28A and 28B. The gap 30 is preferred to be quite narrow compared to the length of rear rib 28. Gap 30 communicates with rear opening 24. This enables the barb to trap the trabeculae acutely during insertion by permitting the trabeculae to enter rear opening 24 through gap 30.

In use, the electrode is inserted tip first into the heart tissue. Movement of the heart, movement of the patient's chest during respiration, and other normal movements have a tendency to push the electrode rearwardly in the direction indicated by the arrow in FIGS. 2 and 3. As the electrode is pushed in the rearward direction, rear rib elements 28A and 28B will eventually come into contact with trabeculae present in the heart tissue.

Because barbs 20 are flexible, as the electrode is pushed in the rearward direction at least one of the rear rib elements, for example, rear rib element 28A, will bend toward the tip 12 as shown in phantom lines in FIG. 2 to admit the trabeculae into rear opening 24. Once the trabeculae have been admitted into rear opening 24, it becomes very difficult to dislodge the probe, since any additional force which would tend to dislodge the electrode (i.e., force in the direction indicated by the arrow in FIGS. 2 and 3) will bring mid-rib 26 into contact with the trabeculae now within rear opening 24, thus preventing further rearward movment of the electrode.

Figure 3:
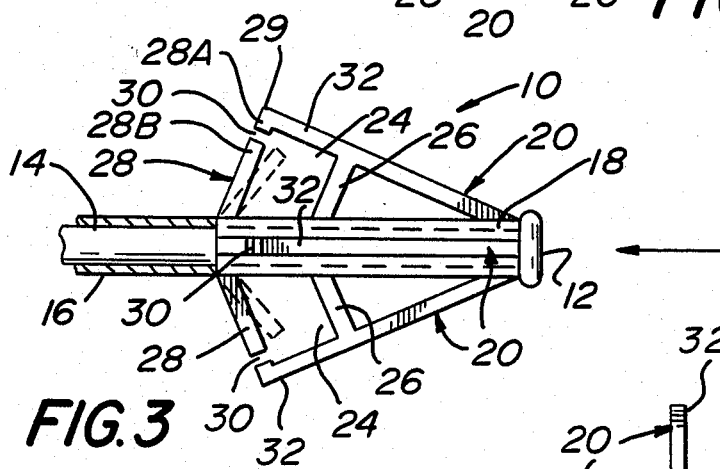
FIG. 3 is a partial cross-section of an alternate embodiment of the invention.

It is believed that the location of gap 30 along the rear rib 28 is not critical to the proper function of the invention. Thus, although gap 30 is shown in FIG. 2 closely adjacent the insulating sheath 16, it is believed that gap 30 may be located in the center of rear rib 28 or even near the elbow 29 between forward arm 32 and rear rib 28, as shown in FIG. 3. In the embodiment shown in FIG. 3, it is expected that at least one of the rear rib elements, for example rear rib element 28B, will bend (as shown in phantom lines) toward the tip 12 to admit trabeculae into rear opening 24.

Once the electrode 10 is in place, it will remain in place as new heart tissue grows around and through openings 22 and 24 to permanently anchor the electrode.

It will be appreciated that the present invention provides a simple but effective way of preventing a pacemaker electrode from becoming dislodged during initial insertion.

The present invention may be embodied in other specific forms without departing from the spirit or essential attributes thereof and, accordingly, reference should be made to the appended claims, rather than to the foregoing specification, as indicating of the scope of the invention.

I claim:

1. In an electrode for insertion into the human heart, the electrode having an electrically conductive contact at an end thereof, a flexible electric conductor connected to the contact a flexible insulating sheath rearward of the contact and encasing the conductor, and at least one flexible barb, each barb comprising an arm connected to said flexible insulating sheath adjacent said contact defining an opening therebetween, the improvment comprising a bifurcated rib comprising a first rib element connected to the arm and a second rib element connected to the sheath, said rib elements being separated by a gap communicating with said opening.

2. In an electrode for insertion into the human heart, the improvement according to claim 1 including a rib connecting said sheath and arm at a location intermediate the contact and the bifurcated rib.

3. In an electrode for insertion into the human heart, the electrode having an electrically conductive contact at an end thereof, a flexible electric conductor connected to the contact, a flexible insulating sheath rearward of the contact and encasing the conductor, and at least one flexible barb, each barb comprising an arm connected to said flexible insulating sheath adjacent said contact defining an opening therebetween, said opening being divided by a mid-rib connecting said arm and sheath, the improvement comprising a bifurcated rib rearward of the mid-rib comprising a first rib element connected to said arm and a second rib element connected to said sheath, said rib elements being separated by a gap communicating with the portion of said opening between said bifurcated rib and the mid-rib.

4. In an electrode for insertion into the human heart, the improvement according to claims 1 or 2 wherein said gap is located proximal to said sheath.

5. In an electrode for insertion into the human heart, the improvement according to claim 1 wherein said gap is located proximal to said arm.

6. In an electrode for insertion into the human heart, the improvement according to claim 1 wherein said gap is located approximately mid-way between the arm and sheath.

* * * * *